(12) United States Patent
Singh

(10) Patent No.: US 9,186,215 B2
(45) Date of Patent: Nov. 17, 2015

(54) MICROWAVE COAPTIVE SURGICAL SEALING TOOL

(71) Applicant: City of Hope, Duarte, CA (US)

(72) Inventor: Gagandeep Singh, Pasadena, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 14/326,736

(22) Filed: Jul. 9, 2014

(65) Prior Publication Data

US 2014/0371738 A1 Dec. 18, 2014

Related U.S. Application Data

(63) Continuation-in-part of application No. 13/928,204, filed on Jun. 26, 2013, which is a continuation-in-part of application No. 13/842,510, filed on Mar. 15, 2013.

(60) Provisional application No. 61/706,603, filed on Sep. 27, 2012.

(51) Int. Cl.
*A61B 18/18* (2006.01)
*A61B 18/14* (2006.01)
*A61B 18/00* (2006.01)

(52) U.S. Cl.
CPC ......... *A61B 18/1815* (2013.01); *A61B 18/1442* (2013.01); *A61B 2018/0063* (2013.01); *A61B 2018/00404* (2013.01); *A61B 2018/00529* (2013.01); *A61B 2018/1823* (2013.01); *A61B 2218/002* (2013.01); *A61B 2218/007* (2013.01)

(58) Field of Classification Search
CPC ........ A61B 17/29; A61B 17/12; A61B 17/42; A61B 17/320016; A61B 17/3201; A61B 18/085; A61B 19/10; A61B 18/1442; A61B 18/1445; A61B 17/072; A61B 18/18; A61B 17/1114; A61B 18/04; A61B 17/2812; B32B 27/08
USPC .......................................... 606/51
See application file for complete search history.

(56) References Cited

U.S. PATENT DOCUMENTS

| | | | | |
|---|---|---|---|---|
| 3,732,719 | A * | 5/1973 | Pallotta | 72/409.01 |
| 4,671,274 | A | 6/1987 | Sorochenko | |
| 5,116,332 | A | 5/1992 | Lottick | |
| 5,300,087 | A * | 4/1994 | Knoepfler | 606/207 |
| 5,395,312 | A | 3/1995 | Desai | |
| 6,010,516 | A | 1/2000 | Hulka | |

(Continued)

OTHER PUBLICATIONS

United States Patent and Trademark Office, Office Action dated Nov. 14, 2014 for U.S. Appl. No. 13/842,510, filed Mar. 15, 2013.
The International Searching Authority International Search Report and the Written Opinion for International Application No. PCT/US2014/022824 (Jul. 1, 2014).

(Continued)

*Primary Examiner* — Robert N Wieland
(74) *Attorney, Agent, or Firm* — Mintz Levin Cohn Ferris Glovsky and Popeo P.C.

(57) ABSTRACT

A coaptive surgical sealing tool may be similar to an ordinary hemostat with long (50, 60, 70 or 80 mm) thin jaws for sliding into the liver parenchyma, without tearing the larger blood vessels. The jaws are spring loaded and are designed for uniform compression, and to avoid closing too quickly. The jaws are capable of sealing a 50, 60, 70 or 80 mm sealing length, in a single bite, although it can also seal shorter lengths as well. The tool can be used with existing ablative therapy microwave generators. The tool may be provided with irrigation and/or suction.

13 Claims, 5 Drawing Sheets

(56) References Cited

U.S. PATENT DOCUMENTS

| | | |
|---|---|---|
| 6,863,669 B2 | 3/2005 | Spitzer |
| 7,422,591 B2 | 9/2008 | Phan |
| 2003/0181910 A1* | 9/2003 | Dycus et al. .................... 606/51 |
| 2005/0159745 A1 | 7/2005 | Truckai et al. |
| 2006/0235379 A1 | 10/2006 | McClurken et al. |
| 2011/0004208 A1* | 1/2011 | Truckai et al. ................. 606/45 |
| 2013/0018411 A1 | 1/2013 | Collings et al. |
| 2013/0296843 A1* | 11/2013 | Boudreaux et al. ............ 606/33 |

OTHER PUBLICATIONS

Aesculap, Inc. (A B. Braun Company), Catalog—"Instruments and Devices for Bipolar Surgery," Sep. 2012.

Aragon Surgical, Inc., "CAIMAN breeds confidence", Lektrafuse CAIMAN product brochure, 3 pages (Jan. 2010).

United States Patent and Trademark Office, Office Action dated Feb. 26, 2015 for U.S. Appl. No. 13/928,204, filed Jun. 26, 2013.

United States Patent and Trademark Office, Office Action dated Mar. 5, 2015 for U.S. Appl. No. 13/842,510, filed Mar. 15, 2013.

* cited by examiner

US 9,186,215 B2

MICROWAVE COAPTIVE SURGICAL SEALING TOOL

CROSS-REFERENCE TO RELATED APPLICATIONS

This Application is a Continuation-in-Part of U.S. patent application Ser. No. 13/928,204 filed on Jun. 26, 2013 and now pending, which is a continuation-in-part of U.S. patent application Ser. No. 13/842,510 filed Mar. 15, 2013 and now pending, which claims priority to U.S. Provisional Patent Application No. 61/706,603, filed Sep. 27, 2012. Each of these applications is incorporated herein by reference.

BACKGROUND OF THE INVENTION

Removal of part of the liver (hepatic resection) is often performed to remove a tumor. Blood loss is a serious complication associated with this procedure. Multiple surgical techniques and devices have been developed to minimize blood loss and improve outcomes in hepatic resection. Several studies including a 2009 Cochrane Systematic Review of techniques for liver parenchymal transection have examined the efficacy of different methods of liver resection. Based on this review, the clamp-crush technique was favored due to low cost and with newer techniques such as cavitron ultrasound surgical aspirator (CUSA), hydrojet, and radio frequency dissecting sealer (RFDS) showing no improvement in morbidity or blood transfusion in comparison to the clamp-crush technique.

The clamp-crush technique generally involves crushing the liver parenchyma using a hemostatic clamp tool to expose small vessels and biliary radicals, which are then divided and sealed via radio frequency (RF) energy provided to the jaws of the tool. Various tools have been proposed for this purpose. However, challenges remain in providing a coaptive surgical sealing tool offering superior performance and efficiency in a simple and low-cost design. It is an object of the invention to provide an improved coaptive surgical sealing tool

BRIEF DESCRIPTION OF THE DRAWINGS

In the drawings, the same element number indicates the same element number in each of the views.

DETAILED DESCRIPTION OF THE DRAWINGS

A coaptive surgical sealing tool may be similar to an ordinary hemostat with long (50, 60, 70 or 80 mm) thin jaws for sliding into the liver parenchyma, without tearing the larger blood vessels. The jaws are spring loaded and are designed for uniform compression, and to avoid closing too quickly. The jaws are capable of sealing a 50, 60, 70 or 80 mm sealing length, in a single bite, although it can also seal shorter lengths as well. The tool can be used with existing RF/bipolar cautery generators, including generators the Triad-Covidean Ligasure Generator, the ConMed generator or the Enseal generator. The tool is suitable for open surgery uses, and may also be adapted for laparoscopic surgery. The tool may be provided in different sizes for different caliber of vessels. In view of its simple design, the tool may be supplied at low cost, as either a reusable or single use unit.

In use, the jaws may be closed with a gradual compression process, with a compression spring acting against the closing movement, to prevent tearing of larger blood vessels. The jaws may a slot and/or ridge, to leave a pre-grooved line for transection after the seal has been completed. The tool may reduce parenchymal transection times in excess of 50%. With 55 mm or more of sealing length it can seal more tissue in one bite than any existing device yet it is also versatile enough to seal small lengths of tissue.

Figure 1:
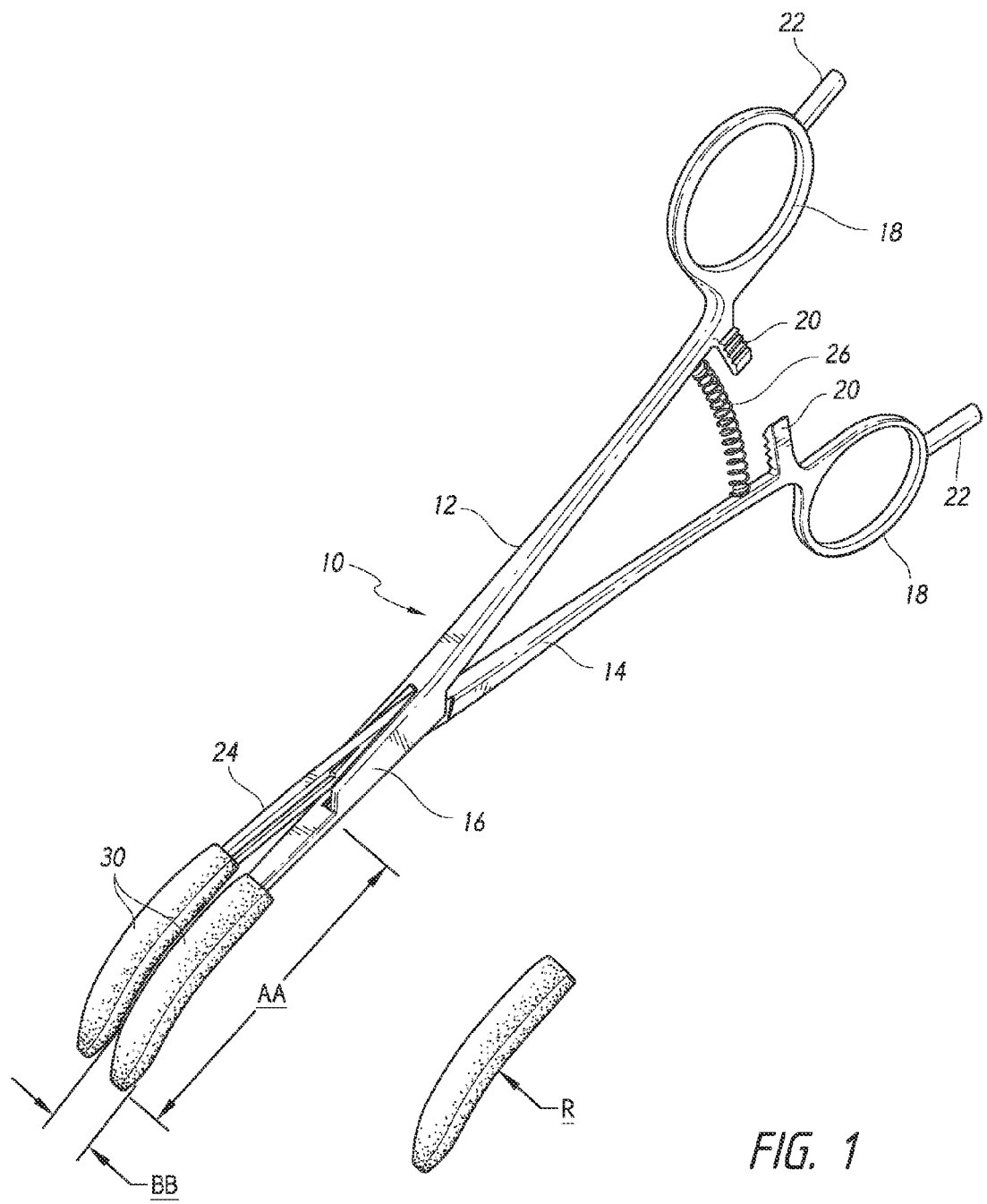
FIG. 1 is a perspective view of a coaptive surgical sealing tool.

As shown in FIG. 1, an example of the tool 10 has first and second arms 12 and 14 pivotally connected via a hinge 16. A finger ring 18 is provided on the back or proximal end of each arm 12, 14. Each arm 12, 14 has a jaw 24 in front or distal of the hinge 16. A spring 26 urges the jaws into an open position. A lock tab 20 may be provided adjacent to each finger ring 18, to allow the jaws 24 to remain clamped or closed, against the force of the spring. The tool 10 according is similar to a hemostat clamp, and consequently benefits from ergonomic design elements of a hemostat clamp. Hence the tool 10 provides ease of use when used in open surgery. Connectors 22 may connect electrodes 30 on the jaws 24 to an RF generator.

The jaws 24 are very thin and easy to slide through the liver parenchyma without disrupting the parenchyma architecture. For example, the jaws may a length AA or 50, 60, 70 or 80 mm, and a width BB of 4, 5, 6 or 7 mm. The spring 26 helps to prevent accidentally closing down on the parenchyma to quickly which prevents parenchymal disruption. The jaws 24 may be straight or curved with a radius R of about 3-10 cm. Typically, the curvature of the jaws, if any, is in the downward direction, i.e., about an axis parallel to the axis of the hinge 16.

The electrodes 30 may extend over the full length of each jaw 24, or only partially over each jaw 24, as shown in FIG. 1. The electrodes 30 may optionally be removable and separately replaceable.

A low cost embodiment of the tool may be provided by modifying a conventional hemostat clamp having long slender jaws, to include the spring 26, the electrodes 30 and connectors 22.

As used for hepatic resection, the surgeon slides the jaws 24 through the liver parenchyma. With the jaws appropriately positioned around a vessel or biliary radical, the jaws 24 are slowly closed via the surgeon squeezing the finger rings 18 towards each other. The electrodes 30 on the inside of the jaws are clamped or pressed onto opposite sides of the vessel. The spring 26 acts against this closing movement, helping to provide a slow and controlled movement. With the tool 10 held momentarily in a fixed position, RF energy is then provided to the electrodes 30, sealing the vessel.

The tool may of course also be used for other surgical procedures on other organs apart from the liver.

From 2010-2012, a total of 51 patients underwent >30% liver resection for malignant disease. All patients underwent open laparotomy for hepatic resection. The patient sample was diverse. The majority of patients underwent resection for metastatic disease to the liver; 4 gallbladder cancer with radical liver resection; 1 hepatocellular carcinoma; 3 patients had documented cirrhosis. Procedures included: 7 patients were combined colorectal primary and liver resection; 2 patients underwent second resection for recurrence; 7 patients had additional nanoknife procedures at the time of resection. Post-op adverse events within 30 days of surgery included 0 bile leaks; 1 blood transfusion; 1 return to operating room for colon anastomatic leak; no intra-abdominal abscess. Use of the present tool as described appears to be a safe and effective technique for major hepatic resection with minimal post-operative adverse events.

During use of a bipolar surgical cautery tool, heat generated by the tool tends to result in char forming on the jaws. Char causes the jaws to stick to the tissue being cauterized, making the surgery more difficult. Char also increases the electrical resistance between the jaws, reducing the cautery effect of the tool. Char can be reduced by supplying an irrigation fluid to the cautery site, reducing the need for frequently stopping the procedure to clean char from the jaws.

Figure 2:
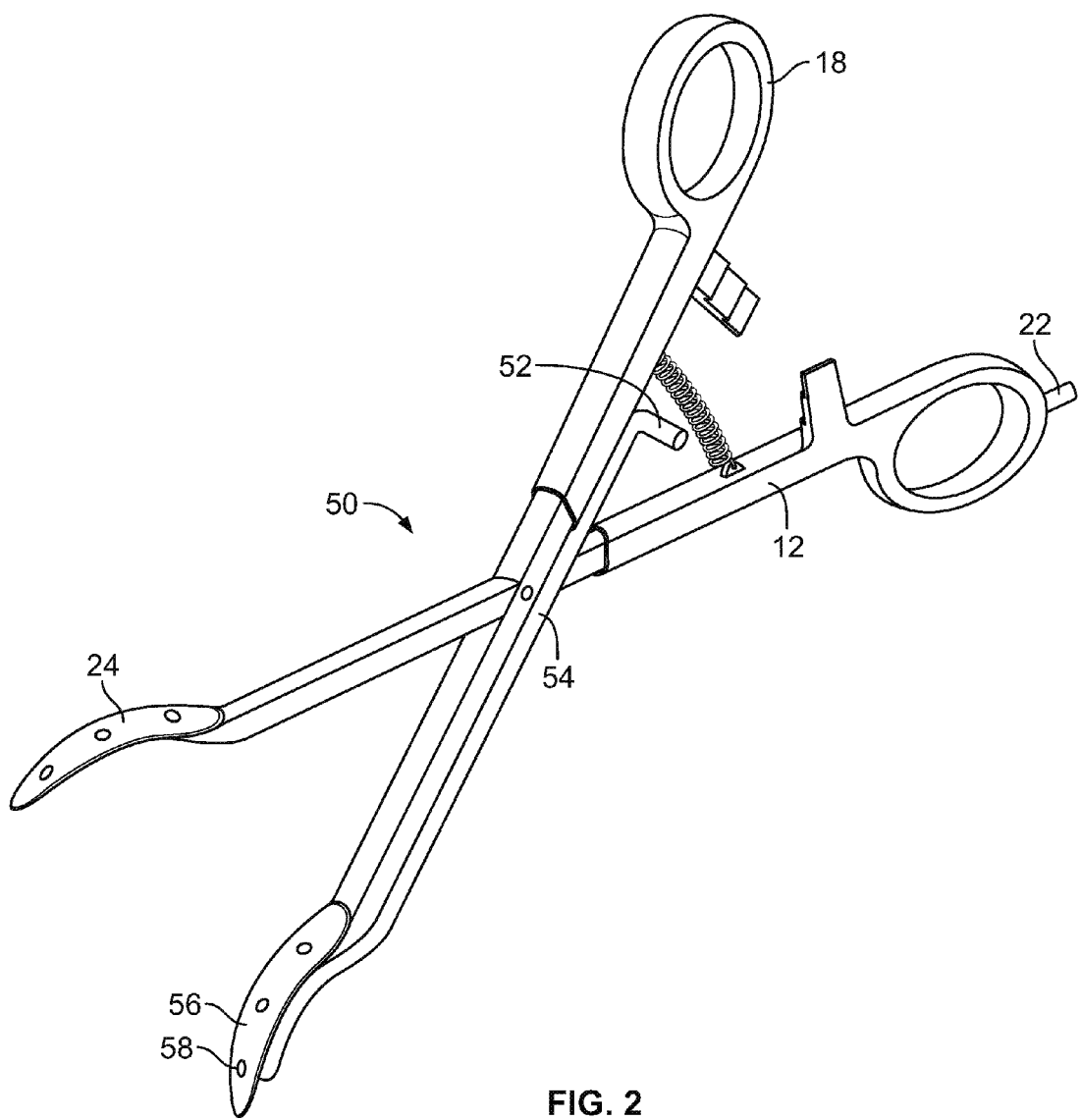
FIG. 2 is a perspective view of another coaptive surgical sealing tool further including irrigation.

As shown in FIG. 2, a bipolar surgical cautery tool 50 may be similar to the tool 10 shown in FIG. 1 and further include irrigation to reduce char. Irrigation may be provided via an irrigation port or fitting 52 adapted for connection to a source of irrigation fluid, such as saline. The irrigation port 52 is connected to an irrigation line 54 on or in the tool leading to the electrode 56. The irrigation line 54 may simply have a single outlet at the electrode 56, or it may have multiple outlets 58 spaced apart along the electrode. The irrigation line 54 may be provided as a flexible tube attached to the tool 50. Alternatively the irrigation line 54 may be provided as an internal duct leading from the arm 12 to the electrode 56.

Figure 4:
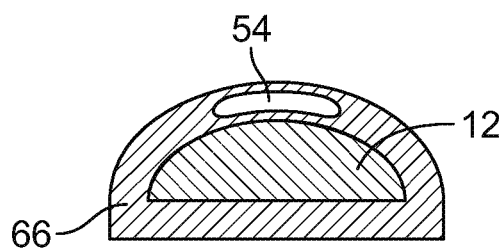
FIG. 4 is an enlarged partial section view design detail of an insulated tool arm providing an irrigation or suction line.
Figure 5:
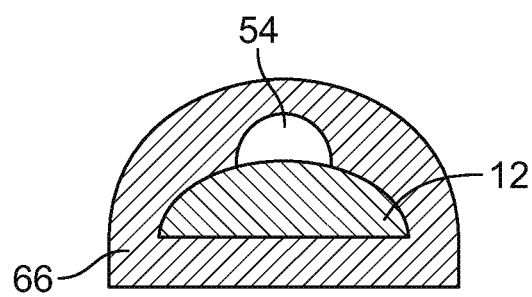
FIG. 5 is an enlarged partial section view alternative design detail of an insulated tool arm providing an irrigation or suction line.

As shown in FIG. 4, in another design, one or both arms 12 may optionally be covered or coated with an insulating material 66, such as plastic or rubber, with the irrigation line 54 formed in insulating material 66. The insulating material may also optionally cover one or both finger rings 18. As shown in FIG. 5, if the insulating material 66 is used, the irrigation line 54 may alternatively be provided as an open flow space between the arm 12 and the insulating material 66.

In use, the source of irrigation fluid connected to the irrigation port 52 may be linked to the RF generator switch so that irrigation fluid flows onto or out of the electrode 56 whenever the switch is on. By applying a constant drip or flow of irrigation liquid during cautery, char build up is reduced.

Figure 3:
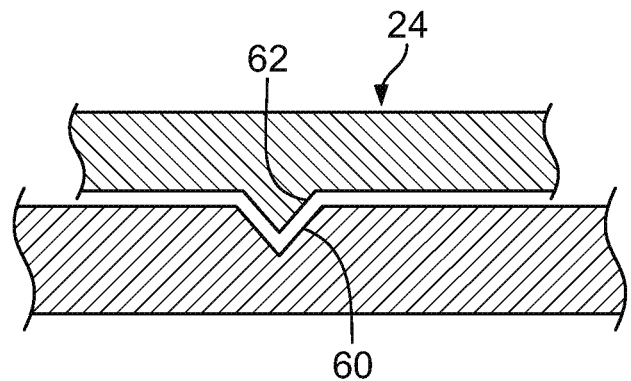
FIG. 3 is an enlarged partial section view design detail of an electrode pair that may be used on the jaws of the tool shown in FIG. 1 or 2.

FIG. 3 shows a modification of the jaw 24 where a projection 62 is provided on the electrode 30 on the upper jaw and a complementary groove 60 is provided on the electrode 30 on the lower jaw. The projection may extend parallel to the longitudinal axis of the arm 24 and typically has a height of 1-3 mm. Consequently, as the upper and lower jaws are brought together, while the electrodes are cauterizing tissue, they also form a pre-grooved line in the tissue for transection, after the seal has been completed.

Figure 6:
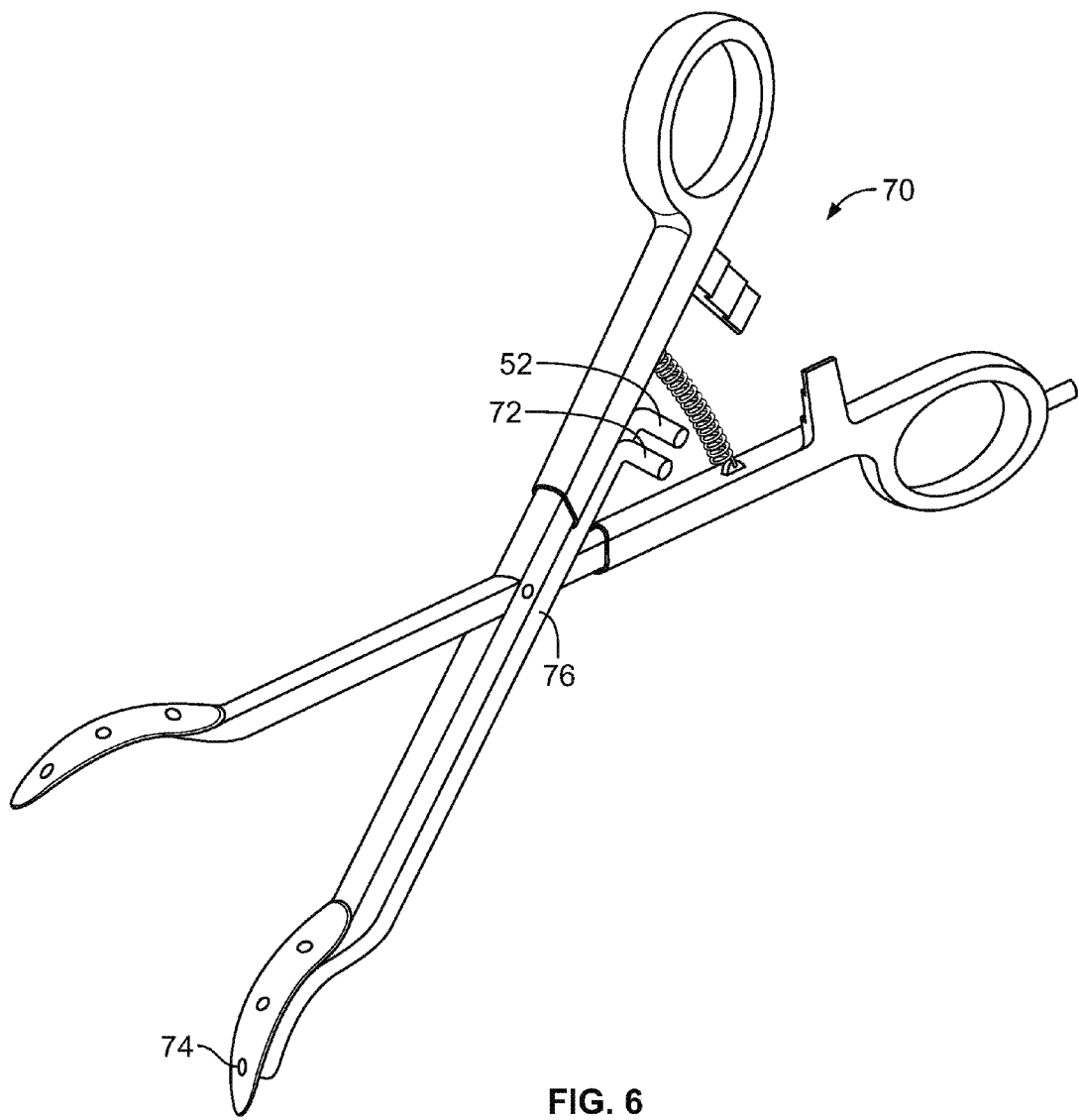
FIG. 6 is a perspective view of an alternative modification of the tool shown in FIG. 2 further including irrigation and suction.

Turning to FIG. 6, a tool 70 may be provided with the same design as the tool 50 shown in FIG. 2, further including suction for helping to remove excess blood and/or irrigation fluid. The tool 70 includes a port or fitting 72 for attachment to a suction source. One or more suction inlets 74 may be provided on one or both electrodes 30 or 58, with the suction inlets 74 connected to a suction line 76 connecting to the suction port 72. The suction line 76 may be designed in the same ways as the irrigation line 54 described above.

Figure 7:
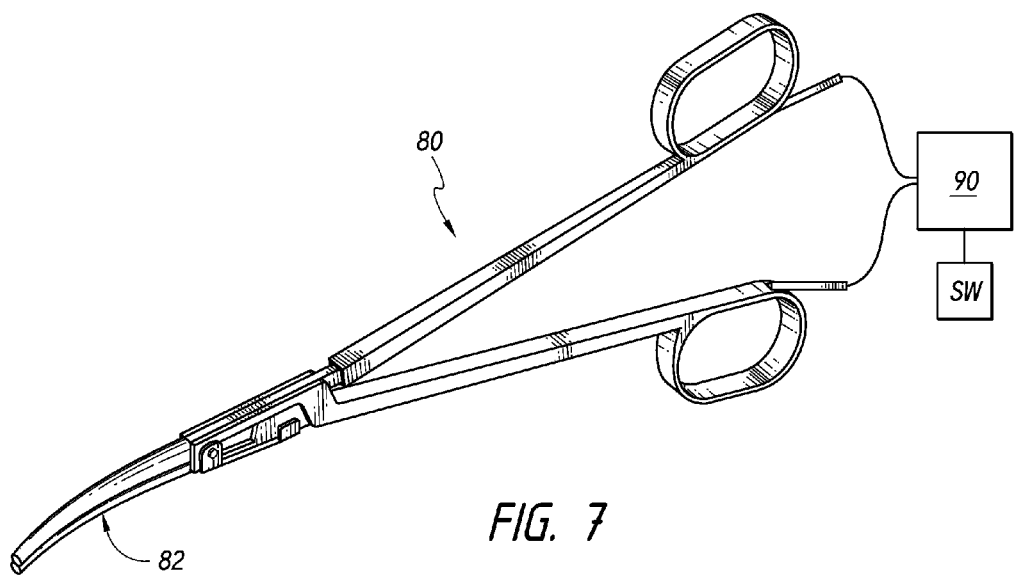
FIG. 7 is a perspective view of another alternative tool design using microwave energy.
Figure 8:
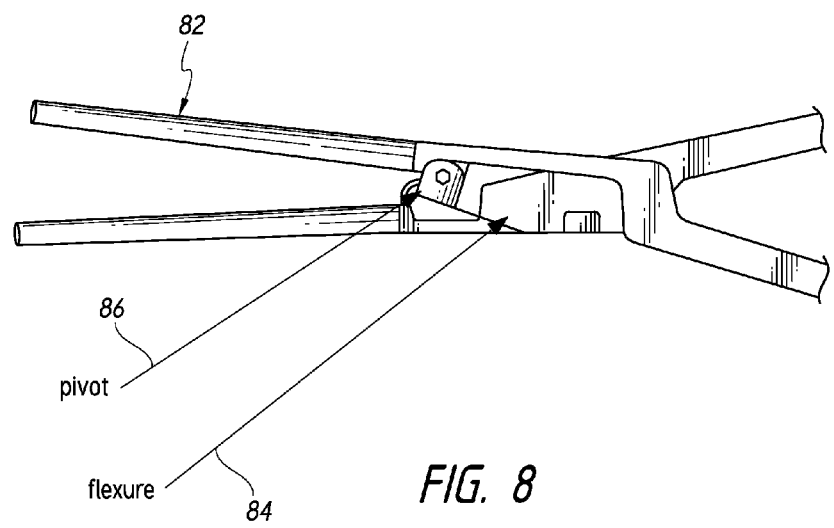
FIG. 8 is an enlarged side view of the jaws of the tool shown in FIG. 7.

Referring to FIGS. 7 and 8, a microwave coaptive vessel sealing tool 80 has long tissue and vessel sealing jaws 82. An alternate energy form i. e., microwave energy may be applied to the jaws from the microwave generator 90, rather than using radio frequency energy, direct current, ultrasound, or other form of energy. Each jaw 82, or an electrode on each jaw, is connected to a surgical microwave generator, e. g., of the type currently used for ablative therapies. The microwave coaptive vessel sealing tool 80 is designed for sustained uniform compression without shearing through the tissue. Gradual pressure may be applied along the jaws resulting in a very good seal of the tissue.

The microwave coaptive vessel sealing tool 80 may be designed to work like an ordinary hemostat. The closure may be a gradual compression process, protected by a spring or flexure resistance element 84 loaded mechanism to prevent tearing of larger blood vessels. The spring 84 may be mounted on or at the pivot connection 86 attaching the jaws to each other. The jaws may be extremely thin (as thin as the existing needles), for example 1, 2 or 3 mm wide, to allow for sliding it in to the liver parenchyma without tearing any of the vessels or tissues. The tools described above with reference to FIGS. 1-6 may also optionally be connected to a microwave generator 90 instead of an RF energy source.

The tool 80 may be provided with an insulated covering with an optional inbuilt irrigation channel. If used, the irrigation channel may provide a steady drip of saline when the microwave switch is activated, to help to prevent the tissue from getting charred and keeping the jaws of the tool 80 clean. Using the tool may leave a pre-grooved line for transection after the seal has been completed. The tool may be capable of reducing parenchymal transection times in excess of 50%. With 55 mm of sealing length, the tool 80 may seal more tissue in one bite than existing devices, while still being versatile enough to seal small lengths of tissue. The tool 80 may be inexpensive to allow it to be used with existing microwave generators.

Thus, novel designs and methods have been shown and described. Various changes and substitutions may of course be made without departing from the spirit and scope of the invention. The invention, therefore, should not be limited, except by the following claims and their equivalents.

The invention claimed is:
1. A surgical tool comprising:
first and second arms, each having a front section and a back section, and with the arms pivotally attached to each other at a pivot connection between the front and back section of each arm;
a spring urging the back sections of the arms away from each other;
first and second jaws on the front section of the first and second arms, respectively;
first and second electrodes on or embodied in the first and second jaws, respectively;
a microwave generator connected via a cable directly or indirectly to the first and second electrodes;
an irrigation port on the first arm connected to an irrigation line leading to one or more irrigation fluid outlets in or adjacent to the first or second electrode; and
a switch connected to the microwave generator and a source of irrigation fluid connected to the irrigation port such that microwave enemy and irrigation fluid are both applied when the switch is activated.
2. The surgical tool of claim 1 with the first and second jaws each having a width of 7 mm, a length of 5 to 8 cm, and a finger ring on the back section of each arm.
3. The surgical tool of claim 1 with the first and second jaws each having a width of 4-6 mm.

4. The surgical tool of claim 1 further comprising first and second connectors electrically connected to the first and second electrodes and adapted to connect to the microwave generator.

5. The surgical tool of claim 1 further including a suction port on the first arm connected to a suction line leading to one or more suction openings in or adjacent to the first or second electrode.

6. The surgical tool of claim 1 further including a longitudinal projection on the first electrode and a complementary groove on the second electrode.

7. The surgical tool of claim 1 with the first and second jaws each having a width of 1-3 mm.

8. A coaptive surgical sealing tool comprising:
   first and second arms, each having a front section and a back section, and with the arms pivotally attached to each other at a pivot connection between the front and back section of each arm;
   a finger ring on the back section of each arm;
   a spring between the back sections of the arms, with the spring urging the back sections of the arms away from each other;
   first and second jaws on the front section of the first and second arms, respectively, with the first and second jaws having a length of 5 to 8 cm and a width of 4-7 mm;
   first and second electrodes on the first and second jaws, respectively;
   first and second connectors electrically connected to the first and second electrodes and adapted to connect to a microwave generator;
   an irrigation port on the first arm connected to an irrigation line leading to one or more irrigation fluid outlets in or adjacent to the first or second electrode;
   a suction port on the first arm or the second arm and connected to a suction line leading to one or more suction openings in or adjacent to the first or second electrode; and
   a switch connected to the microwave generator and a source of irrigation fluid connected to the irrigation port such that microwave energy and irrigation fluid are both applied when the switch is activated.

9. The coaptive surgical sealing tool of claim 8 with the first and second jaws each having a width of 1-3 mm.

10. A surgical method, comprising:
    sliding the jaws of a surgical hemostat clamp-type of tool through a liver parenchyma;
    positioning the jaws around a vessel;
    closing the jaws to press first and second electrodes on the inside of the jaws onto opposite sides of the vessel;
    applying microwave energy to the electrodes to seal the vessel;
    applying an irrigation fluid onto the vessel in the jaws; and
    closing a switch to apply the microwave energy, with the switch also controlling application of the irrigation fluid.

11. The method of claim 10 with the irrigation liquid applied through one or more openings in the first electrode.

12. The method of claim 10 further including applying suction adjacent to the jaws.

13. The method of claim 10 with the jaws each having a width of 1-3 mm.

* * * * *